(12) United States Patent
Myung et al.

(10) Patent No.: US 9,377,426 B2
(45) Date of Patent: Jun. 28, 2016

(54) SELECTIVE NANOSCALE ASYMMETRIC GAS SENSORS

(71) Applicant: THE REGENTS OF THE UNIVERSITY OF CALIFORNIA, Oakland, CA (US)

(72) Inventors: Nosang V. Myung, Riverside, CA (US); Lauren Brooks, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 176 days.

(21) Appl. No.: 14/082,349

(22) Filed: Nov. 18, 2013

(65) Prior Publication Data

US 2014/0145736 A1    May 29, 2014

Related U.S. Application Data

(60) Provisional application No. 61/727,181, filed on Nov. 16, 2012.

(51) Int. Cl.
  *G01N 27/26* (2006.01)
  *G01N 27/12* (2006.01)

(52) U.S. Cl.
  CPC ................... *G01N 27/129* (2013.01)

(58) Field of Classification Search
  CPC .................... G01N 27/4146; G01N 27/16
  USPC ........................ 324/693, 464, 71.1
  See application file for complete search history.

(56) References Cited

U.S. PATENT DOCUMENTS

| | | | | |
|---|---|---|---|---|
| 5,457,333 A * | 10/1995 | Fukui | ...................... | G01N 27/16 257/252 |
| 5,814,281 A * | 9/1998 | Williams | ............... | G01N 27/12 422/83 |
| 8,529,124 B2 * | 9/2013 | Kaul | .................... | G01N 27/127 374/1 |
| 2009/0085071 A1 * | 4/2009 | Brongersma | ...... | G01N 27/4146 257/253 |
| 2010/0193375 A1 * | 8/2010 | Liemersdorf | ...... | G01N 27/4141 205/775 |

OTHER PUBLICATIONS

Yang et al., "Carbon nanotube Schottky diode and directionally dependent field-effect transistor using asymmetrical contacts", App. Phys. Lett. 87, 253116 (2005).
Chen et al., "Chemical Fabrication of Heterometallic Nanogaps for Molecular Transport Junctions", Nano Letter, vol. 9, No. 12, 2009, pp. 3974-3979.
Mueller et al., "Graphene photodetectors for high-speed optical communications", Nature Photonics, vol. 4, May 2010, pp. 297-301.
Haeng et al., "Selective CO Gas Detection of Zn2SnO4 Gas Sensor", Journal of Electroceramics, 8, 2002, pp. 249-255.

(Continued)

*Primary Examiner* — Vincent Q Nguyen
(74) *Attorney, Agent, or Firm* — Buchanan Ingersoll & Rooney PC

(57) ABSTRACT

A selective nanoscale asymmetric gas sensor is disclosed, the sensor including a first electrode having a Schottky-type contact to a nanoengineered transducer with a barrier height between energy levels of the first electrode and the nanoengineered transducer; and a second electrode having an Ohmic contact to the nanoengineered transducer with a smaller or no barrier height than the first electrode. The first electrode can be palladium and the second electrode can be gold.

14 Claims, 3 Drawing Sheets

(56) References Cited

OTHER PUBLICATIONS

Fang et al., "Electronic transport properties of carbon chains between Au and Ag electrodes: A first-principles study", Physics Letters A 375 (2011), pp. 3618-3623.

Deshmukh et al., "Fabrication of Asymmetric Electrode Pairs with Nanometer Separation Made of Two Distinct Metals", Nano Letters, vol. 3, No. 10, 2003, pp. 1383-1385.

Szabo et al., "Microporous zeolite modified yttria stabilized zirconia (YSZ) sensors for nitric oxide (NO) determination in harsh environments", Sensors and Actuators B 82 (2002), p. 142-149.

* cited by examiner

SELECTIVE NANOSCALE ASYMMETRIC GAS SENSORS

CROSS REFERENCE TO RELATED APPLICATION(S)

This application claims priority under 35 U.S.C. §119(e) to U.S. provisional application No. 61/727,181, filed on Nov. 16, 2012, the entire contents of which is incorporated herein by reference in its entirety.

FIELD

The present disclosure relates to gas sensors, and more particularly to selective nanoscale asymmetric gas sensors.

BACKGROUND

To date, most chemiresistive gas sensors have been made using source and drain electrodes of the same material. With this construction, the signal response output of the sensor can be the same regardless of the direction of current flow in the sensor, a result of the polarity of the applied bias voltage during gas exposure. Some work has been done with electrodes of unequal surface areas but identical materials, or with dissimilar materials but different sensing mechanisms other than chemiresistive-type sensors.

SUMMARY

In accordance with an exemplary embodiment, a selective nanoscale asymmetric gas sensor is disclosed, the sensor comprising: a first electrode having a Schottky-type contact to a nanoengineered transducer with a barrier height between energy levels of the first electrode and the nanoengineered transducer; and a second electrode having an Ohmic contact to the nanoengineered transducer with a smaller or no barrier height than the first electrode.

In accordance with another exemplary embodiment, a method of detecting a gas is disclosed, the method comprising: providing a selective nanoscale asymmetric gas sensor, the gas sensor comprising: a first electrode having a Schottky-type contact to a nanoengineered transducer with a barrier height between energy levels of the first electrode and the nanoengineered transducer; and a second electrode having an Ohmic contact to the nanoengineered transducer having a smaller or no barrier height than the first electrode; applying an alternating voltage to the first and the second electrode; and comparing signals from the first and second electrodes, which are generated by the alternating voltage to identify one or more gases.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DETAILED DESCRIPTION

One-dimensional nanostructure based chemiresistive sensors have received great attention because of their compact design and excellent sensing performance including high sensitivity, low detection limits, low power consumption, and ability to integrate multi-sensor arrays. However, the current state-of-the-art sensor technology uses identical source and drain electrodes in sensor construction. To improve the selectivity, a systematic sensor was designed where the source and drain electrodes are made from different materials. These asymmetric sensors possess source and drain electrodes of identical geometry, but dissimilar materials (e.g. gold and palladium). By alternating the applied voltage bias between positive and negative during gas exposure, the direction of current flow will alter which electrode is the source and drain (for example, if there is a positive bias then the palladium electrode is the source electrode, but a negative bias means the gold electrode is the source electrode). In addition, by changing the bias of the sensor, the signal output can reflect the behavior typical of the metal that is the source electrode. In accordance with an exemplary embodiment, these two different signal outputs from the same sensor, reflecting the two bias directions, can then be compared to eliminate cross-sensitivity and interference.

Figure 3:
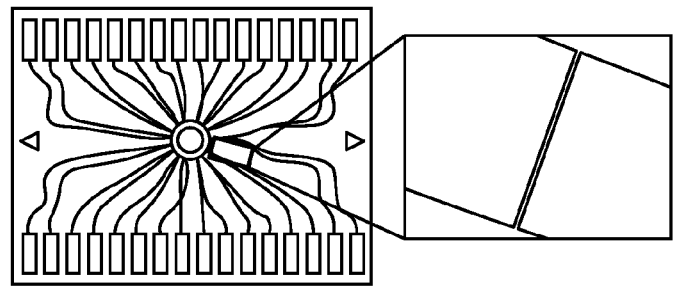
FIG. 3 shows an asymmetric Pd and Au microfabricated electrodes, with inset of high magnification optical image of the electrodes.

In accordance with an exemplary embodiment, it would be desirable to have a sensor construction that is a chemiresistive-type sensor with electrodes of identical geometry but different electrode materials as shown in FIG. 3, so that positive and negative bias will produce different responses upon exposure to an analyte.

Figure 1:
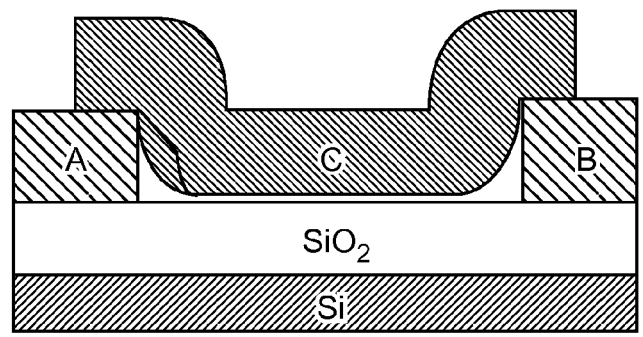
FIG. 1 shows a schematic representation of an exemplary chemiresistor construction, including microfabricated electrodes (A and B) and nanoengineered transducer (C)
Figure 2:
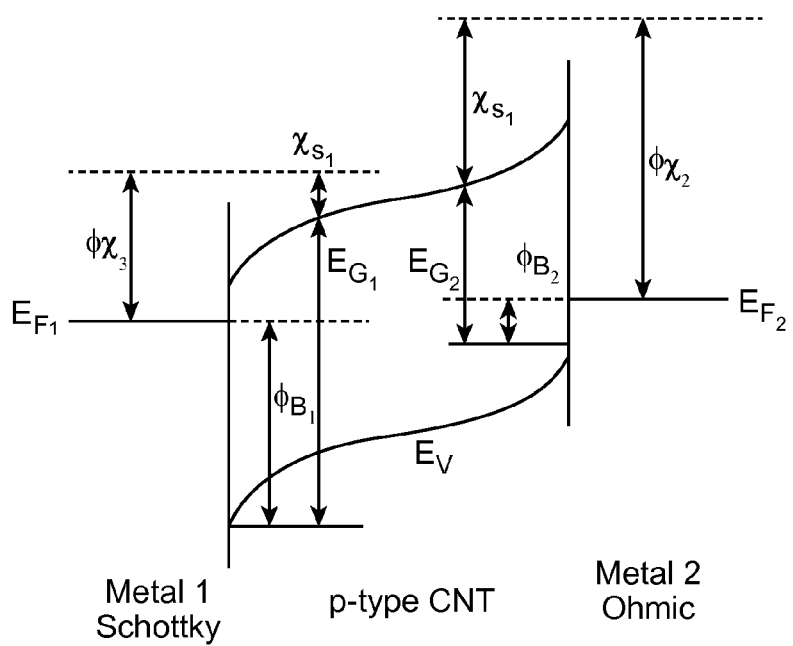
FIG. 2 shows an energy band diagram of an asymmetric sensor, wherein Metal 1 to nanoengineered transducer is a Schottky contact and metal 2 to nanoengineered transducer is an Ohmic contact $\phi_B$: Schottky barrier; $\phi_M$: metal work function; $E_F$: Fermi level; $E'_V$: valence band; $E_G$: Transducer band gap; $\chi_s$: Transducer electron affinity.

In accordance with an exemplary embodiment, a schematic band diagram of an asymmetric sensor is shown in FIG. 2, with an electrode (Metal 1) having a Schottky-type contact to the nanoengineered transducer, for example, single walled carbon nanotubes, (FIG. 1C) with a substantial barrier height between the energy levels of the electrode and the nanotubes. In accordance with an exemplary embodiment, the other metal electrode can be an Ohmic contact with a small or no barrier height. Adsorbed gas molecules on the electrode surfaces can change the work functions of the metals, thus raising or lowering the Fermi level in each metal. For example, changes in the Fermi level alter the height of the energy barrier between the electrode and the transducer can alter the amount of the current that can flow through the sensor and producing a likewise variable, measurable response to gas exposures. For example, different metals have different work function energies, as well as varying affinities for various gases, both of which affect the sensor performance towards a particular gas.

Figure 4:
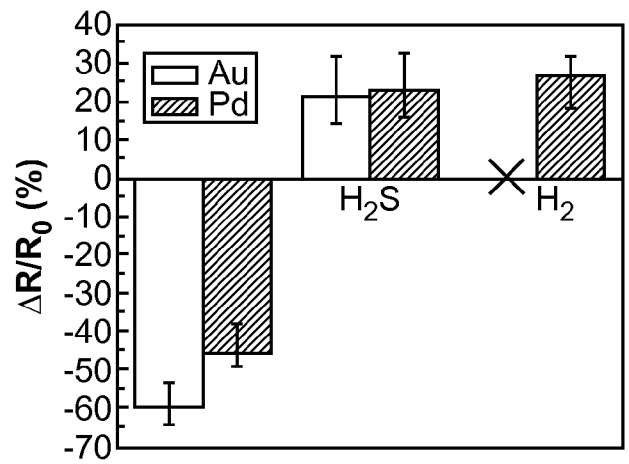
FIG. 4 shows a sensing responses of Au and Pd sensors in $NO_2$ (5 ppm$_v$), $H_2S$ (20 ppm$_v$), and $H_2$ (1000 ppm$_v$), and wherein X represents no measurable response.

In accordance with an exemplary embodiment, an asymmetric sensor was fabricated, which included an array of 15 asymmetric sensors and a reference electrode as shown in FIG. 3. Each sensor consisted of one palladium electrode and one gold electrode. For example, the responses of symmetric chemiresistive sensors with identical material composition of both electrodes to several different gases were measured. However, some metals showed similar magnitudes of responses to different gases. An example is shown in FIG. 4, which found that sensors with palladium electrodes produced comparable magnitudes of responses to both hydrogen sulfide and hydrogen gases. The responses to nitrogen dioxide, while of a very different magnitude, also produce comparable responses. Thus, if a palladium sensor was operating in the field and showed a 25% response, identification of the triggering gas as hydrogen or hydrogen sulfide would be very difficult. However, by creating an asymmetric sensor, different responses from a single sensor were produced depending on the polarity of the applied bias.

Figure 5:
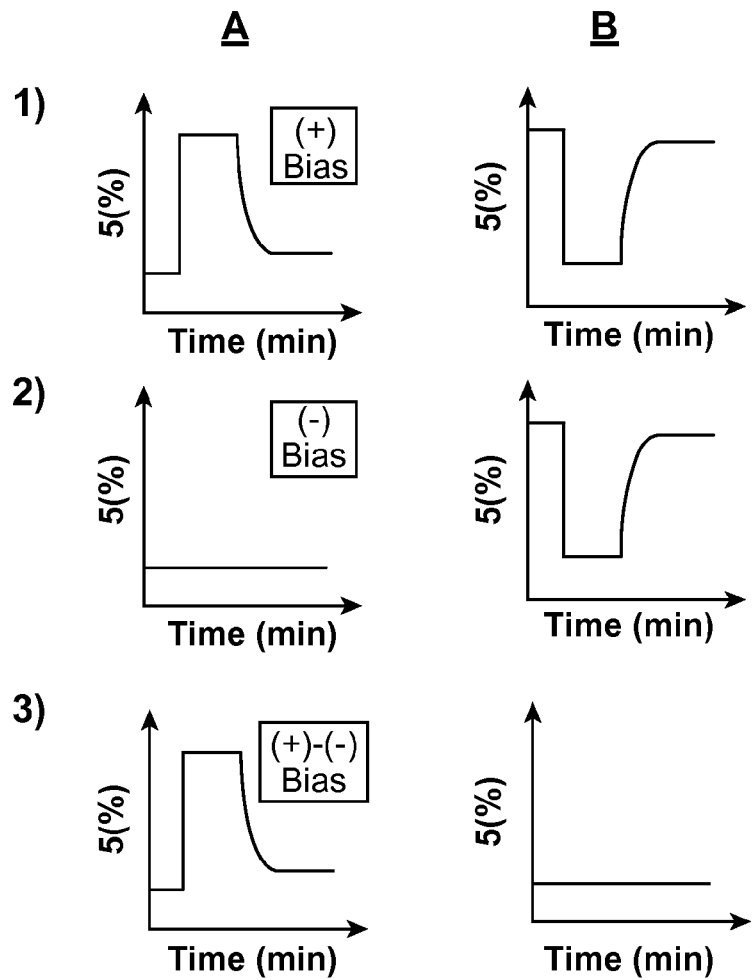
FIG. 5 shows a conceptual representation of sensing responses of an asymmetric sensor with a positive bias (row 1), a negative bias (row 2), and the difference between the responses (row 3), and wherein Column A represents exposures to a single gas, such as $H_2$, and column B a second gas, such as $NO_2$.

For example, by comparing difference between the magnitudes of the two responses, one is able to identify the analyte gas producing the sensor response. In accordance with an exemplary embodiment, this is illustrated conceptually in FIG. 5, where sensor responses to gases A and B produce either very different or similar responses depending on the polarity of the bias voltage (positive for row 1, negative in row 2). If the two responses are very different, as for gas A, with a large response in the positive direction and a negligible response in the negative direction, the difference between the two signals (A3) resembles the strong response from the positive response. Conversely, for gas B, both bias directions produce signals of similar magnitude, resulting in a combined signal (B3) that is small to negligible.

For example, a metal that produces signals to multiple gases, such as palladium in FIG. 4 to hydrogen and hydrogen sulfide, can be paired on a sensor with a metal that has different responses to the same gases. Then by comparing the responses from both applied biases (FIG. 5, row 3) the sensor will show a response to one gas (A3), but no measurable response to a second gas (B3), eliminating the cross-sensitivity of one of the metal electrodes (1A and 1B) to more than one gas.

For example, when a sensor is exposed to multiple gases simultaneously, as is normally the case in conditions outside of a controlled laboratory setting, the identity of the gases detected by the sensor can be easily identified.

Figure 6:
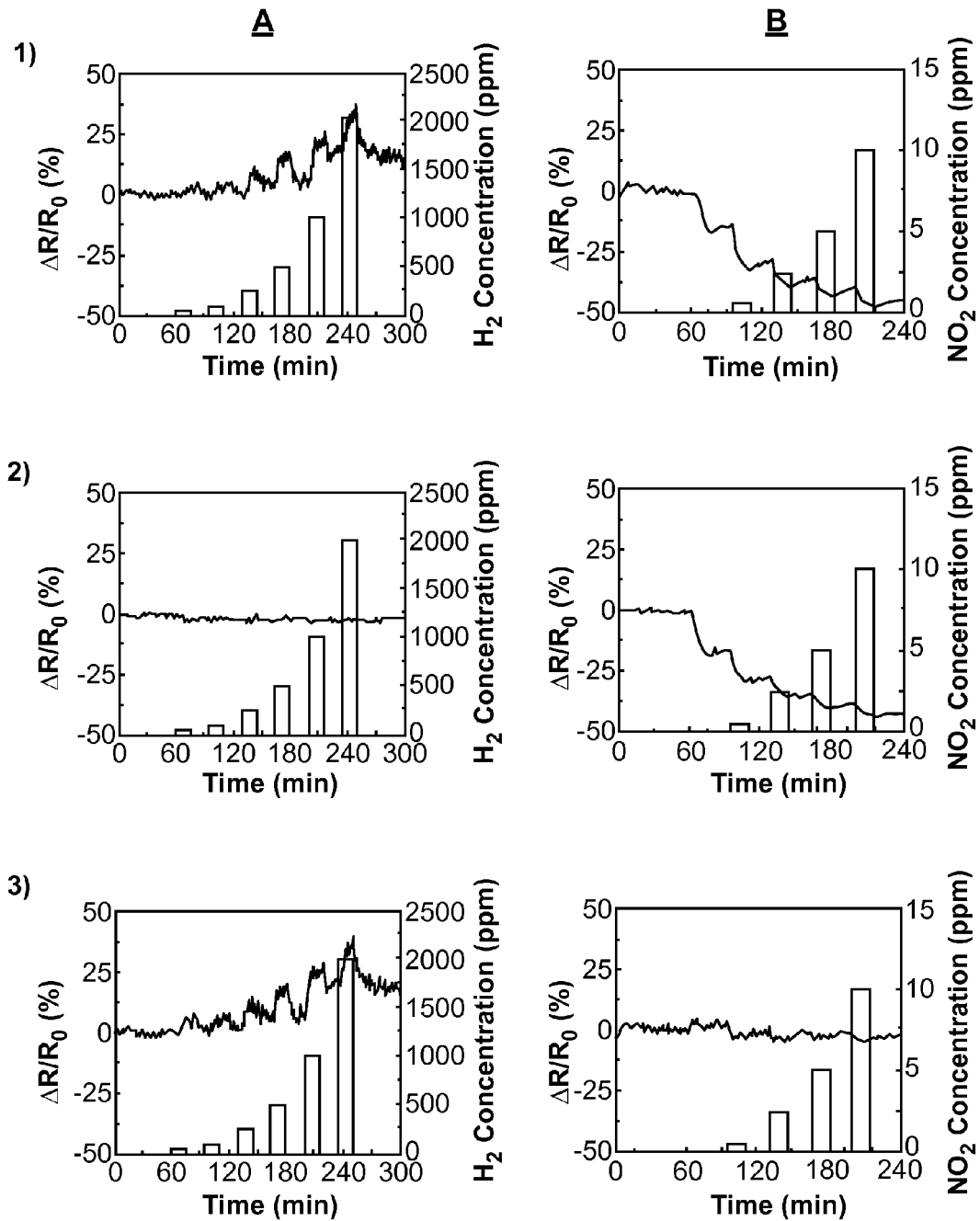
FIG. 6 shows real-time sensing responses of a single asymmetric Au/Pd sensor at +1 and −1 V applied biases (rows 1 and 2, respectively), and the overall sensor response of the negative bias subtracted from the positive one (row 3), and wherein the gases detected are $H_2$ (column A) and $NO_2$ (column B).

In accordance with an exemplary embodiment, an Au/Pd sensor of the type from FIG. 3 was fabricated, and real-time sensing data was obtained as shown in FIG. 6. In accordance with an exemplary embodiment, two separate sensing experiments were conducted, one at a positive applied bias of 1 V and the other at a negative bias of −1 V. As seen from the sensing results, at a positive bias the current direction was such that the palladium electrode was the source electrode, which was where the current entered, and the gold electrode was the drain electrode where the current left. For example, for hydrogen, column A, the response in this direction was very similar to the results for the symmetric palladium sensors as shown in FIG. 3. The negative bias direction showed the opposite results, with the gold electrode as the source electrode and the palladium as the drain, and the magnitude of the response like that of the symmetric gold electrode to hydrogen. Taking the difference of the two responses and comparing it to the difference in responses of the symmetric sensors from FIG. 4, one can conclude that the difference in the magnitude of the responses was the same for both the symmetric and asymmetric sensors. Column B compares the responses of the two sensors to nitrogen dioxide, where there is little difference between the two biases as shown in B3. This ability to compare two different signals from one sensor simply by changing the polarity of the applied bias voltage gives us a powerful new tool for identifying gases outside of a laboratory setting where the identity of the gases being exposed to the sensor may not be known.

The invention is not limited, however, to the embodiments and variations described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A one-dimensional selective nanoscale asymmetric gas sensor, the sensor comprising:
   a first electrode having a Schottky-type contact to a nanoengineered transducer with a barrier height between energy levels of the first electrode and the nanoengineered transducer;
   a second electrode having an Ohmic contact to the nanoengineered transducer with a smaller or no barrier height than the first electrode; and
   wherein the first and the second electrodes have identical geometries and are made from different electrode materials.

2. The sensor of claim 1, wherein the nanoengineered transducer is a single walled carbon nanotube.

3. The sensor of claim 1, wherein the first electrode is palladium and the second electrode is gold.

4. The sensor of claim 1, comprising:
   an alternating applied voltage to the first and the second electrodes.

5. The sensor of claim 4, comprising:
   an applied bias of +1 V.

6. The sensor of claim 4, comprising:
   an applied bias of −1 V.

7. The sensor of claim 1, comprising:
   an array of asymmetric sensors, each sensor of the array of asymmetric sensors consisting of one palladium electrode and one gold electrode.

8. A method of detecting a gas, the method comprising:
   exposing a gas to a one-dimensional selective nanoscale asymmetric gas sensor, the gas sensor comprising:
      a first electrode having a Schottky-type contact to a nanoengineered transducer with a barrier height between energy levels of the first electrode and the nanoengineered transducer;
      a second electrode having an Ohmic contact to the nanoengineered transducer having a smaller or no barrier height than the first electrode; and
      wherein the first and the second electrodes have identical geometries and are made from different electrode materials;
   applying an alternating voltage to the first and the second electrode; and
   comparing signals from the first and second electrodes, which are generated by the alternating voltage to identify one or more gases.

9. The method of claim 8, wherein the first electrode is palladium and the second electrode is gold.

10. The method of claim 8, wherein the applied alternating voltage is an applied bias of +1 V.

11. The method of claim 8, wherein the applied alternating voltage is an applied bias of −1 V.

12. The method of claim 8, comprising:
exposing the gas to an array of asymmetric sensors, each sensor of the array of asymmetric sensors consisting of one palladium electrode and one gold electrode.

13. The method of claim 8, wherein the one or more gases is $NO_2$, $H_2S$, or $H_2$.

14. The method of claim 8, comprising:
measuring a Fermi level in the first and second electrodes.

* * * * *